United States Patent [19]

Inchiosa et al.

[11] Patent Number: 5,898,035
[45] Date of Patent: Apr. 27, 1999

[54] FORMULATIONS OF HALOALKYLAMINES AND LOCAL ANESTHETICS AND METHODS FOR THE TREATMENT OF REFLEX SYMPATHETIC DYSTROPHY (RSD)

[75] Inventors: Mario Inchiosa, Woodclif Lake, N.J.; Kamil Mustafa, Bronxville, N.Y.

[73] Assignee: New York Medical College, Valhalla, N.Y.

[21] Appl. No.: 08/727,624

[22] PCT Filed: Aug. 28, 1996

[86] PCT No.: PCT/US96/14061

§ 371 Date: Oct. 22, 1996

§ 102(e) Date: Oct. 22, 1996

[87] PCT Pub. No.: WO97/07793

PCT Pub. Date: Mar. 6, 1997

Related U.S. Application Data

[60] Provisional application No. 60/002,899, Aug. 29, 1995.

[51] Int. Cl.$^6$ ...................... A61K 31/135; A61K 31/165; A61K 31/24
[52] U.S. Cl. .......................... 514/626; 514/537; 514/651; 514/655
[58] Field of Search .................................. 514/537, 626, 514/651, 655

[56] References Cited

U.S. PATENT DOCUMENTS

| | | | |
|---|---|---|---|
| 5,070,084 | 12/1991 | Campbell | 514/248 |
| 5,260,313 | 11/1993 | Frome | 514/552 |

OTHER PUBLICATIONS

Bonica, J.J.:Causalgia and Other Reflex Sympathetic Dystrophies in *The Management of Pain*. Philadelphia, Lea & Febiger, I: pp. 220–243, 1990.

Omer, G.E. and M. Spinner: Management of Peripheral Nerve Problems. Philadelphia, W.B. Saunders Co., pp. 216–244, 1980.

Schwartzman, R.J. and T.L. McLellan.:Reflex Sympathetic Dystrophy in *Arch. Neurol.*, 44:pp. 555–561, May 1987.

Wall, P.D. and R. Melzack.:Antisympathetic Drugs in Limbs in *Textbook of Pain*. London, Churchill Livingstone, pp. 566–573, 1984.

Blanchard, J.S., N.W. Ramamurthy, J. Hoffman and L. Schoenfeld.:Intravenenous Regional Sympatholysis: a Double–Blind Comparison of Guanethidine, Reserpine and Normal Saline in *Journa l of Pain and Symptom Management*. 5(6):pp. 357–361, 1990.

Jadad, A.R., D. Carroll, C.J. Glynn and H.J. McQuay.:Intravenous Regional Sympathetic Bloackade for Pain Relief in Reflex Sympathetic Dystrophy:A Systematic Review and A Randomized, Double–Blind Crossover Study in *Journal of Pain and Symtom Management*. New York, U.S. Cancer Pain Relief Committee, 10(1):pp. 13–20, January 1995.

Ghostine, S.Y., Y.G. Comair, D.M. Turner, N.F. Kassell and C.G. Azar.:Phenoxybenzamine in the Treatment of Causalgia in *J. Neurosurg.*60:pp. 1263–128, 1984.

Ikeda, M.:Effect of Phenoxybenzamine on Portal Venous Pressure in Patients with Portal Hypertension in *Amer. J. Gastroenterology*. 71:pp. 389–394, 1979.

Aguirre, A., C.G. Axpe and J.P. Vinas.: Distrofia Simpatica Refleja en la Infancia in *An. Esp. Pediatr*. 34(1):74–76, 1991.

Blanchard, J., S. Ramamurthy, N. Walsh, J. Hoffman and L. Schoenfeld.:Intravenous Regional Sympatholysis:A Double–Blind Comparison of Guanethidine, Reserpine, and Normal Saline in *Journal of Pain and Symptom Management*. New York, U.S. Cancer Pain Relief Committee, 5(6):pp.357–361,1990.

Cooke, E.:Reflex Sympathetic Dystrophy in *Vascular Medicine Review*. 5:pp. 319–330, 1994.

Cooke, E.D. and C. Ward.:Vicious Circles in Reflex Sympathetic Dystrophy–A Hypothesis:Discussion Paper in *Journal of the Royal Society of Medicine*. 83:pp.96–99, February 1990.

Dzwierzynski, W.W. and J.R. Sanger.:Reflex Sympathetic Dystrophy in *Complications of Common Hand Procedures*. 10(1):pp. 29–44, February 1994.

Goodman, L.S. and A. Gilman.:Pharmacological Basis of Therapeutics. New York, MacMillan, pp. 183–187;190–191 and 213, 1985.

Hannington–Kiff, J.G.:Antisympathetic Drugs in Limbs in *Textbook of Pain*. New York, Churchill Livingstone, pp. 566–573, 1984.

Hannington–Kiff, J.G.: Pharmacological Target Blocks in Painful Dystrophic Limbs in *Textbook of Pain*. New York, Churchill Livingstone, pp. 754–766, 1989.

(List continued on next page.)

*Primary Examiner*—Phyllis G. Spivack
*Attorney, Agent, or Firm*—Robert S. MacWright; Evelyn M. Sommer

[57] ABSTRACT

The present invention pertains to the field of pain management in medicine. Methods for treating reflex sympathetic dystrophy (including causalgia) are provided, in which a haloalkylamine a adrenergic blocking agent and a local anesthetic are administered to the affected limb by intravenous regional block. Formulations which can be used in these methods are also provided. In a preferred embodiment, phenoxybenzamine and either lidocaine or procaine are administered to the affected limb using a Bier block procedure.

20 Claims, No Drawings

OTHER PUBLICATIONS

Kozin, F.:Reflex Sympathetic Dystrophy Syndrome:A Review in *Radiology*. 1990(3):pp 652,1994.

Mandel, S. and R.W. Rothrock.:Sympathetic Dystrophies–Recognizing and Managing A Puzzling Group of Syndromes in *Postgraduate Medicine*. 87(8): pp.213–214; 217–218, June 1990.

Murray, P. and R. Atkinson.:Reflex Sympathetic Dystrophy in *British Journal of Hospital Medicine*. 53(1/2): pp.35–57; 39–40, 1995.

Paalzow, G.H.M.: Nordadrenaline But Not Dopamine Involved in NMDA Receptor–Mediated Hyperalgesia Induced by the Ophylline in Awake Rates in *European Journal of Pharmacology*. 252: pp. 87–97, 1994.

Rocco, A.G.: The Evolution of a Technique for Managing Sympathetically Maintained Pain in *Regional Anesthesia*. 20(1): p. 3–12, 1995.

Schepelmann, K., U.W. Buettner and J. Dichgans.:Therapie der Sympthischen Reflex Dystrophie in *Munch, Med. Wschr.*136(19):pp.47–48; 51–52, 1994.

Sizemore, G.W. and W.W. Winternitz.:Autonomic Hyper–Reflexia–Suppression with Alpha–Adrenergic Blocking Agents in *New Engel J. Med.* 282(14):pg.795, 1970.

Derwent Drug File Abstracts, Volume 23, No. 10, issued 1988, Fine, P.G. "The Pharmacologic Management of Sympathetically Maintained Pain", Abstract No. 88–48702, Hosp. Formal. 23(10), 796–808.

Derwent Drug File Abstracts, Volume 71, No. 3A, issued 1989, Arias L M et al, "Investigation of Labetalol Injections at Sympathetic Ganglia for the Treatment of Reflex Sympathetic Dystrophy", Abstract No. 89–477221, Anesthesiology, 71(3A), A735.

FORMULATIONS OF HALOALKYLAMINES AND LOCAL ANESTHETIC AND METHODS FOR THE TREATMENT OF REFLEX SYMPATHETIC DYSTROPHY (RSD)

This application claims priority to U.S. Provisional Application 60/002,899 filed Aug. 29, 1995. The entire text of that application is incorporated herein by reference.

This case is a 371 of PCT/US96/14061 filed Aug. 28, 1996.

FIELD OF THE INVENTION

The invention pertains to the field of pain management in medicine. More specifically, the invention pertains to the field of managing and treating the pain and other symptoms resulting from the disorder known as reflex sympathetic dystrophy (RSD).

BACKGROUND ART

Reflex Sympathetic Dystrophy, or "RSD," is a common but poorly recognized chronic syndrome that most often occurs following traumatic injury to a limb. It is also associated with heart attack (myocardial infarction) and certain disorders of the nervous system. RSD includes disorders that were in the past known as causalgia, minor causalgia, post-traumatic pain syndrome, post-traumatic spreading neuralgia, post-traumatic vasomotor disorders, post-traumatic painful arthrosis, Sudeck's atrophy, sympathalgia, shoulder-hand syndrome, chronic traumatic edema, post-traumatic edema, autonomic hyper-reflexia, and reflex dystrophy, among others. (See: Bonica, J. J., *The Management of Pain*, Second Ed., Lea & Febiger, Philadelphia, 1990, pp. 220–243). The International Association for the Study of Pain continues to distinguish "causalgia," which is a more severe disorder often caused by nerve injury from war-inflicted shrapnel or projectile wounds, and which has some distinctive symptoms such as psychological disturbances that apparently result from the continuous, intense pain. However, most clinicians and researchers recognize that causalgia is symptomologically quite similar to the reflex sympathetic dystrophies, that it is treated in essentially the same way, and that it likely results from the same underlying mechanisms. Therefore, we hereinafter use the terms reflex sympathetic dystrophy and "RSD" to mean all of the above-mentioned disorders, including causalgia, as well as other disorders that fall within the symptomological definition of RSD.

RSD causes pain, stiffness, disturbances of the limb's blood vessels and muscles, and swelling. It is generally disabling because of the intensity of the pain. Also, since movement of the affected limb makes the pain much worse, patients suffering from RSD often stop using the affected limb at all. (Lankford, L. L., Reflex Sympathetic Dystrophy, in: *Management of Peripheral Nerve Problems*, G. E. Omer, Jr., and M. Spinner, eds; W. B. Saunders Co., Philadelphia, 1980; pp. 216–244.)

RSD often occurs following sprains, dislocations, and fractures of the hands, feet or wrists, and also following traumatic amputation of fingers, hands or wrists. However, the likelihood of developing RSD and its severity cannot be predicted based upon the severity of the injury; the disorder can even be caused by seemingly minor injuries such as contusions, cuts or even pinpricks to the fingers, hands, toes or feet. Following heart attacks, some patients develop a form of RSD known as "shoulder-hand syndrome," where the shoulder becomes painful and disabled, and the hand on the same side becomes painful and swollen.

Although many theories have been advanced, the mechanism that causes RSD is not clearly understood. One recent view is that RSD is caused by increased firing of peripheral nerves due to increased sensitivity, which in turn causes altered responses by the spinal cord, which then responds abnormally to signals from the brain stem and cortex. (See: Schwartzman, R. J. and T. L. McLellan, Reflex Sympathetic Dystrophy, *Arch. Neurol.* 44:555–561).

Unless successfully treated, RSD progresses through three stages of increasing disability. In Stage I, the "acute" phase, there is a burning or aching pain that is greater than the pain caused by the initial injury. The pain gets worse when the limb is touched, or when the patient becomes emotionally upset. The limb becomes swollen, hot or cold to the touch, and there is pronounced hair and nails growth. In Stage II, the "dystrophic" phase, the limb becomes hard and swollen, sweaty, and cool, and the hair begins to fall out. The nails become ridged, cracked and brittle. The pain becomes constant, and is increased by any stimulation of the limb. In Stage III, the "atrophic" stage, the pain spreads from the limb, and irreversible tissue damage occurs. The skin becomes thin and shiny, and the fingertips become wasted. The fingers may become permanently flexed, and X-rays show considerable bone loss. Id.

An important method for treating RSD is to temporarily block the sympathetic nerves of the affected limb. The sympathetic nerves are those that largely contain adrenergic fibers (i.e., those that use norepinephrine as a neurotransmitter), and which tend to depress secretion, decrease the tone and contractility of visceral smooth muscles, and cause the contraction of blood vessels. Such a blockade can be accomplished by injecting a local anesthetic such as lidocaine into the symapthetic nerve ganglia near the spinal cord that serve the affected limb. More commonly today, however, this is accomplished by making a local anaesthetic block of the affected limb. This is done by using a "Bier block." A Bier block is performed by elevating the limb and isolating it from the circulation using a tourniquet; the anesthetic is then injected into the limb intravenously, and left there for five to fifteen minutes. The tourniquet is then removed. This provides an effective sympathetic blockade, but without the inherent risks involved in injecting spinal ganglia.

Such regional local anesthetic blocks can be quite effective in treating RSD, particularly when carried out early in the course of the disorder. The response is generally prompt and dramatic; the anesthetic blocks the sympathetic nerves and also relaxes vascular smooth muscle, resulting in vasodilation and a reversal of the pain. The administration of repeated blocks over a period of time often improves the relief provided. It has been optimistically reported that such blockades combined with vigorous physical therapy can effect a "cure" for about 80% of patients with RSD. Binica, Supra. However, there are still at least 20% of patients who do not obtain complete relief. In addition, even among those who might otherwise obtain substantially complete relief by this method, good results depend upon prompt treatment.

Another method of considerable interest is the use of intravenous regional sympathetic block (IRSB) with the specific sympathetic nerve terminal blocking drug guanethidine. (IRSB is another term used to describe what is essentially a Bier block using a drug other than a local anaesthetic). Hannington-Kiff, J. G., "Antisympathetic drugs in limbs," in: *Textbook of Pain*, P. D. Wall and R. Melzak, eds., Churchill Livingstone, London, (1984), pp. 566–573. Guanethidine is a drug which displaces norepinephrine in presynaptic vesicles and prevents its reuptake.

Many clinicians have reported good results and the achievement of long lasting pain relief using guanethidine IRSB. However, two double-blind comparisons failed to find any statistically significant difference between IRSB with guanethidine and IRSB with salt water (saline), calling into question the value of this therapy. Blanchard, J., S. Ramamurthy, N. Walsh, J. Hoffman, and L. Schoenfeld, "Intravenous Regional Sympatholysis: a Double-Blind Comparison of Guanethidine, Reserpine, and Normal Saline," *Journal of Pain and Symptom Management* (1990) 5(6):357–361; Jadad, A. R., D. Carroll, C. J. Glynn, and H. J. McQuay, "Intravenous Regional Sympathetic Blockade for Pain Relief in Reflex Sympathetic Dystrophy: A Systematic Review and a Randomized, Double-Blind Crossover Study," *Journal of Pain and Symptom Management* (1995) 10(1):13–20.

A third and more recent treatment for RSD is the oral administration of phenoxybenzamine, a potent drug which blocks postsynaptic $\alpha^1$ receptors and also blocks presynaptic $\alpha^1$ receptors. In the primary study of this therapy, increasing oral doses of this drug were administered to RSD patients until a maximum dosage of 40 to 120 mg was reached. This treatment was continued for 6 to 8 weeks. A complete cure was reported for all patients, and the authors concluded that treatment with oral phenoxybenzamine was simple, safe and effective. Ghostine, S. Y., Y. G. Comair, D. M. Turner, N. F. Kassell, and C. G. Azar, "Phenoxybenzamine in the Treatment of Causalgia," *J. Neurosurg.* (1984) 60:1263–1268. However, the authors reported that postural hypotension was a prominent side effect, which caused lightheadedness, and required some patients to wear leg stockinettes or an abdominal girdle throughout treatment. 17 out of 40 patients, or about 45%, were reported to have experienced hypotension. Some patients also reported ejaculatory problems. These side effects, particularly in view of the need to continue therapy for 6 to 8 weeks, substantially reduces the value of oral phenoxybenzamine for the treatment of RSD.

DISCLOSURE OF THE INVENTION

Although Bier blockade with local anesthetics can be effective in many patients, there is a need for therapies that can be tried when this fails to provide a cure. Unfortunately, as described above, the available alternative therapies are less than ideal. IRSB with guanethidine is of questionable value, as it does not appear to provide any benefit over use of placebos; and oral phenoxybenzamine causes undesirable side effects over a long course of treatment. The objectives of the present invention are to overcome these and other limitations of the prior art.

One object of the present invention, then, is to provide an alternative therapy for RSD that does not cause serious side effects such as hypotension.

Another object of the invention is to provide a therapy that gives measurable therapeutic benefit to RSD sufferers.

Yet another object of the present invention is to provide a therapy that is fast, and thus does not require the continuous ingestion of powerful drugs.

An additional object of the present invention is to provide a therapy that provides active drug to only the affected limb, thus limiting systemic exposure to the drug used.

A further object of the invention is to provide a therapy that may offer greater relief from RSD in a greater proportion of patients than presently available therapies.

In considering the above-described needs, we came to consider whether phenoxybenzamine might be administered by using a Bier-type block. Phenoxybenzamine is primarily used as a blood pressure lowering drug, and we found that phenoxybenzamine is only available in oral dosage forms in the United States. However, we learned that phenoxybenzamine was available outside the United States in an intravenous dosage form. This dosage form was apparently intended for use in treating high blood pressure, as several articles have reported on the use of injectable phenoxybenzamine for its blood pressure effects. See, e.q., Ideda, M., "Effect of Phenoxybenzamine on Portal Venous Pressure in Patients with Portal Hypertension," *Amer. J. Gastroenterology* 71:389–394 (1979). However, we were aware of no reports on the use of intravenous phenoxybenzamine for the treatment of RSD.

Upon inquiry of the manufacturer, we learned that phenoxybenzamine must be injected into the bloodstream very slowly, and in diluted form; otherwise, it causes a severe burning pain. This was discouraging, as the short period for a Bier type block requires fairly rapid administration of the drug.

It was our wish to overcome this problem that led us to conceive of the first embodiment of the present invention: to co-administer phenoxybenzamine and a local anaesthetic via IRSB. We conceived that administering phenoxybenzamine along with a local anaesthetic would potentially provide two benefits: it would provide the therapeutic effects generally obtained when RSD is treated with local anesthetics alone using a Bier block; and the anaesthetic effects on nerve endings would prevent or limit the burning caused by the phenoxybenzamine. As the compound phenoxybenzamine is one of a class of compounds known as haloalkylamine α adrenergic blocking agents, the use of other haloalkylamine α adrenergic blocking agents in conjunction with local anesthetics in IVSB for the treatment of RSD is also within the scope of the present invention.

MODES FOR CARRYING OUT THE INVENTION

Phenoxybenzamine is more generally described as a haloalkylamine α adrenergic blocking agent. Dibenamine is another member of this class of compounds. The haloalkylamines are unique α adrenergic receptor blocking agents in that they form covalent (irreversible) bonds with α adrenergic receptors, thereby causing prolonged blockage of adrenergic transmission to the vasculature of the treated limb. Transmission is blocked until there is resynthesis of receptors in the vasculature, which appears to take several days, a week, or more. None of the other currently available alpha-adrenergic receptor antagonists have this property; they act through reversible interactions with the receptors. As a result, their effects diminish as the drug is cleared by the circulation (a time frame of hours, at most).

We believe that the prolonged blockage produced by haloalkylamines will favor the interruption of the heightened sympathetic reflex that is present in the RSD syndrome, which appears to be the basis for the ischemia and pain. The improved blood perfusion of the affected limb during the days that the haloalkylamine is producing vasodilation (as a result of sympathetic blockade),may help reverse some of the pathological processes that were sustaining the sympathetic reflex. The present invention takes advantage of the benefits offered by the prolonged action of these drugs, but without necessitating systemic exposure that can lead to postural hypotension and other side effects.

The present invention is directed to formulations for the intravenous regional sympathetic blockade treatment of reflex sympathetic dystrophy, comprising a haloalkylamine α adrenergic blocking agent and a local anaesthetic. There are many such formulations that could be made, all of which would be within the scope of the present invention. For example, phenoxybenzamine or dibenamine might be selected as the haloalkylamine a adrenergic blocking agent, or some other haloalkylamine, such as a chemical derivative of phenoxybenzamine and dibenamine. Those of ordinary skill in the art will appreciate that there are other known haloalkylamines that could be used, or that new ones discovered in the future would also be suitable for use in the formulations of the present invention. In addition, there is a very wide spectrum of local anesthetics from which to choose. For example, the formulations of the present inventions might be comprised of procaine, bupivacaine, chloroprocaine, cocaine, cyclomethylcaine, dibucaine, dimethisoquin, dyclonine, hexylcaine, lidocaine, mepivacaine, phenacaine, piperocaine, pramoxine, prilocaine, proparacaine, tetracaine, procaine hydrochloride, bupivacaine hydrochloride, chloroprocaine hydrochloride, cocaine hydrochloride, cyclomethylcaine hydrochloride, dibucaine hydrochloride, dimethisoquin hydrochloride, dyclonine hydrochloride, hexylcaine hydrochloride, lidocaine hydrochloride, mepivacaine hydrochloride, phenacaine hydrochloride, piperocaine hydrochloride, pramoxine hydrochloride, prilocaine hydrochloride, proparacaine hydrochloride, tetracaine hydrochloride, cyclomethylcaine, cyclomethylcaine sulfate, benzocaine, butyl aminobenzoate, orthoform, naepaine, naepaine hydrochloride, benzoxinate, or benzoxinate hydrochloride. Of course, those of ordinary skill in the field will appreciate that there may be other local anesthetics known or to be discovered which would also be suitable for use in the formulations of the present invention. A formulation containing phenoxybenzamine and lidocaine is a most preferred embodiment of the invention.

The formulations of the present invention can be readily optimized by those in the field, through a simple testing program in which different dosages are used with different patients, to determine which works best in the broadest population of patients. Alternatively, one could begin therapy with given patients using a formulation containing relatively low dosages of the haloalkylamine and the local anaesthetic, and then increase dosages in subsequent treatments until sufficient relief is obtained. Such adjustments in dosage are well within the ordinary skill in the art.

As an initial guide, we believe that the formulations of the present invention should preferably contain the haloalkylamine α adrenergic blocking agent in a concentration of about 0.05 to about 1.0 milligrams per milliliter and the local anaesthetic in a concentration of about 0.1% to 0.5% by weight. Of course, all dosages in between would be equally preferred; so, for example, the haloalkylamine could be present in concentrations of 0.5, 0.1, 0.15, 0.2, 0.25, 0.3, 0.35, 0.4, 0.45, 0.6, 0.65, 0.7, 0.75, 0.8, 0.85, 0.9, 0.95, and 1.0 milligrams per milliliter, or other intermediate amounts. Similarly, the local anaesthetic could be present in concentrations of 0.1, 0.15, 0.2, 0.25, 0.3, 0.35, 0.4, 0.45, or 0.5 percent by weight, or at another intermediate concentration. In a particularly preferred embodiment, phenoxybenzamine is present in a concentration of about 0.05 to about 1.0 milligrams per milliliter, and the local anaesthetic is present in a concentration of about 0.1% to 0.5% by weight. In a most preferred embodiment, phenoxybenzamine is present in a concentration of about 0.1 to 0.35 milligrams per milliliter, and lidocaine or procaine is present in a concentration of about 0.2% to 0.4% by weight.

As will be readily appreciated by those of ordinary skill in the field, it is not necessary that only a single haloalkylamine be used, or that only a single local anaesthetic be used. Combinations of these could readily be used, and such combinations would be well within the scope of the present invention.

The present invention also comprises a method for the treatment of reflex sympathetic dystrophy by intravenously co-administering a haloalkylamine α adrenergic blocking agent and a local anaesthetic to the affected limb. Protocols for performing Bier blocks are well known, as are the protocols used in IRSB, e.g., using guanethidine, and these procedures or adaptations of them should be suitable for carrying out the methods of the present invention. The examples given below illustrate one such procedure, but those in the field could readily identify other suitable procedures. The only requirement is that the administration of the drug initially be limited to the affected limb, which is most typically accomplished by the application of a tourniquet before administration of the drug, which prevents the drug from being carried away by the circulation. Of course, the tourniquet must be released after a suitable period, in order to restore blood flow necessary for the limb to survive, and even rather short application of the tourniquet should be sufficient to carry out the invention. A period of fifteen to twenty minutes would be preferred, in order to allow for good drug penetration, yet avoid any complications that might be caused by too long of an interruption in blood supply to the limb.

The methods of the present invention can be carried out using any of the formulations of the present invention, as described above. Preferably, a formulation is administered in a quantity that will provide about 1.5 to about 30 milligrams of the haloalkylamine, and about 30 to 250 milligrams of the local anaesthetic. Most preferably, the formulation administered will provide about 5 to about 10 milligrams of the alkylamine (preferably phenoxybenzamine), and about 75 to about 125 milligrams of the local anesthetic (preferably lidocaine or procaine). Of course, the methods of the present invention could also be carried out using solutions of haloalkylamine and/or local anesthetics that might not fall within the formulations defined herein. For example, one might administer a highly concentrated admixture of haloalkylamine and local anaesthetic either immediately before or immediately after the administration of a quantity of normal saline. Or, one might administer a lidocaine solution and then immediately thereafter administer a solution of haloalkylamine. These and many other variations that would be apparent to those of ordinary skill in the art would be well within the scope of the methods of the present invention.

Preferred quantities of the formulation to be administered to an affected arm would be about 20 to 40 milliliters, with 30 milliliters being most preferred. Preferred quantities of solution to be administered to an affected leg would be somewhat higher, about 40 milliliters to about 60 milliliters, or most preferably about 50 milliliters.

In yet another embodiment of the invention, the local anesthesia is administered first, using, for example, a Bier block protocol. The tourniquet is then released, and the blood flow to the limb is allowed to return to normal. Then, sometime during the period of anesthesia produced by that treatment, preferably within an hour or so, a second block is performed using a solution containing the haloalkylamine. This sequential procedure would be expected to provide comparable clinical results to those discussed above.

In considering the following examples and claims, it is important to recall that as stated above, the terms "regional sympathetic dystrophy" and "RSD" have been used here to include a variety of disorders that have been variously defined in the past. It is most important to note that although the International Association for the Study of Pain continues to distinguish "causalgia," here we have included causalgia within the scope of the terms "regional sympathetic dystrophy" and "RSD." The reason for this is that causalgia is so closely related to RSD in symptoms and treatment that the present invention is just as applicable to causalgia as it is to the IASP recognized forms of RSD.

All other terms and phrases used herein are intended to have the same meaning as generally understood by those in the art. For clarity, some of these are defined below.

The term "haloalkylamines" has been used herein to mean "haloalkylamine α adrenergic blocking agents," which would include, for example, phenoxybenzamine and dibenamine.

The term "sequential" means that two actions are taken one after the other; for example, two drugs administered sequentially would be administered one after the other.

The terms "Intravenous regional sympathetic blockade treatment" and "IRSB" have generally been used herein in relation to sympathetic blockades where blocking agents are administered using Bier-type procedures, such as that described in Example 2 below. However, these terms are not limited to Bier-type procedures, or any particular protocols; those in the field will appreciate that there are many variations in how blocking agents might be intravenously administered to a region of the body, such as a limb, and all such procedures would be encompassed by these terms.

The term "co-administration" is used to indicate that two drugs are administered together. Although this would generally be accomplished by administering an admixture of the drugs, it could also be accomplished by administering one drug right after the other, for example, into an intravenous catheter. (Because the delivery of a concentrated haloalkylamine such as phenoxybenzamine might cause a burning sensation, one would most likely prefer to administer the local anesthetic first).

The term "arm" is intended to include the hand, the forearm, the upper arm, the hand and forearm together, the forearm and the upper arm together, and the hand, forearm and upper arm together. Similarly, the term "leg" is intended to include the foot, the lower leg, the thigh, the foot and lower leg together, the lower leg and thigh together, and the foot, lower leg and thigh together.

The following examples are provided to illustrate the present invention, but should not be construed to limit the scope of the invention in any way.

All references cited herein are incorporated by reference.

EXAMPLE 1

A formulation according to the present invention can be prepared as follows. First, 15 ml of 0.5% lidocaine solution is drawn up into a 50 ml syringe. The plunger is then withdrawn slightly to allow space to add 0.1 ml (5 mg) of phenoxybenzamine solution using a tuberculin syringe and needle. Sterile saline is then drawn into the syringe to provide a total volume of 30 ml, and the contents of the syringe are then be mixed. Such a mixture can be prepared aseptically in the treatment room, immediately before use, by an attending or resident anesthesiologist.

EXAMPLE 2

The following clinical procedure for performing a method of the present invention was adapted from that described by Hannington-Kiff, Supra.

1. A 23 gauge butterfly needle is introduced into a vein on the dorsal surface of the hand or foot of the treated limb. (Another butterfly needle is introduced into a free hand to facilitate the injection of a sedative and to provide access to a vein for safety's sake should a reaction occur to the drugs used in the block). If the veins are thready, the extremity should be filled with saline to prevent a blockage by a blood clot in the period before the agents are introduced through them. Such a 30 ml quantity of the formulation would then be used for intravenous regional sympathetic blockade of an arm, for example, using the protocol provided below.

2. A thin layer of padding is wrapped around the limb and the correct size of tourniquet cuff is carefully applied and secured. The limb is raised well above heart level for about 60 seconds to drain the venous blood and the tourniquet is inflated to at least 50 mm and 100 mmHg above systolic pressure in the case of the arm and leg, respectively. In the sedated patient, higher pressures can be used in the tourniquet. In the upper extremity the site of the tourniquet is usually the upper arm, though the forearm can be used. When less tissue is isolated, the dose of drugs can be reduced without loss of effect. For instance, digits can be isolated and their veins cannulated if causalgia is limited to a distal phalanx. In the lower limb, the tourniquet is not applied to the calf because of the risks of deep vein thrombosis and pulmonary embolism.

3. The limb is returned to the horizontal position and the anesthetic solution is injected at the rate it will conveniently pass from a 50 ml syringe through a 23 gauge butterfly needle. The total volume of solution is approximately 30 ml for the upper limb and 50 ml for the lower limb.

4. The distribution of the drugs in the limb can be hastened by brief periods of active or passive movements of the extremity. After a minimum period of 15 min, the tourniquet is released; it is kept in place, ready to be reinflated, for about 3–4 min. Patients are confined to bed until they are completely ambulatory, as discussed below.

INDUSTRIAL APPLICABILITY

The present invention is applicable in the medical industry. More specifically, it is applicable in the treatment of patients suffering from RSD, by physicians and other qualified medical professionals.

We claim:

1. A pharmaceutical formulation for the intravenous regional sympathetic blockade treatment of reflex sympathetic dystrophy, comprising a haloalkylamine α adrenergic blocking agent and a local anesthetic wherein said haloalkylamine α adrenergic blocking agent is present in a concentration of about 0.05 to about 1.0 milligrams per milliliter and said local anesthetic is present in a concentration of about 0.1% to 0.5% by weight.

2. The formulation of claim 1 wherein said haloalkylamine α adrenergic blocking agent is selected from the group consisting of phenoxybenzamine and dibenamine.

3. The formulation of claim 1 wherein said local anesthetic is selected from the group consisting of procaine, bupivacaine, chloroprocaine, cocaine, cyclomethylcaine, dibucaine, dimethisoquin, dyclonine, hexylcaine, lidocaine, mepivacaine, phenacaine, piperocaine, pramoxine, prilocaine, proparacaine, tetracaine, procaine hydrochloride, bupivacaine hydrochloride, chloroprocaine hydrochloride, cocaine hydrochloride, cyclomethylcaine hydrochloride, dibucaine hydrochloride, dimethisoquin hydrochloride, dyclonine hydrochloride, hexylcaine hydrochloride, lidocaine hydrochloride, mepivacaine hydrochloride, phenacaine hydrochloride, piperocaine hydrochloride, pramoxine hydrochloride, prilocaine hydrochloride, proparacaine hydrochloride, tetracaine hydrochloride, cyclomethylcaine, cyclomethylcaine sulfate, benzocaine, butyl aminobenzoate, orthoform, naepaine, naepaine hydrochloride, benzoxinate, and benzoxinate hydrochloride.

4. The formulation of claim 3 wherein said local anesthetic is selected from the group consisting of procaine, procaine hydrochloride, tetracaine, tetracaine hydrochloride, cocaine, cocaine hydrochloride, chloroprocaine, chloroprocaine hydrochloride, proparacaine, proparacaine hydrochloride, piperocaine, piperocaine hydrochloride, hexylcaine, hexylcaine hydrochloride, naepaine, naepaine hydrochloride, benzoxinate, benzoxinate hydrochloride, cyclomethylcaine, cyclomethylcaine hydrochloride, cyclomethylcaine sulfate, lidocaine, lidocaine hydrochloride, bupivicaine, bupivicaine hydrochloride, mepivicaine, mepivacaine hydrochloride, prilocaine, prilocaine hydrochloride, dibucaine and dibucaine hydrochloride.

5. The formulation of claim 3 wherein said local anesthetic is selected from the group consisting of pramoxine, pramoxine hydrochloride, dimethisoquin, dimethisoquin hydrochloride, phenacaine, phenacaine hydrochloride, dyclonine, and dyclonine hydrochloride.

6. The formulation of claim 3 wherein said local anesthetic is selected from the group consisting of benzocaine, butyl aminobenzoate, and orthoform.

7. A pharmaceutical formulation for the intravenous regional sympathetic blockade treatment of reflex sympathetic dystrophy comprising phenoxybenzamine and a local anesthetic selected from the group of lidocaine and procaine wherein said phenoxybenzamine is present in a concentration of about 0.05 to about 1.0 milligrams per milliliter, and said local anesthetic is present in a concentration of about 0.1% to 0.5% by weight.

8. The formulation of claim 7 wherein said local anesthetic is lidocaine.

9. The formulation of claim 7 wherein said phenoxybenzamine is present in a concentration of about 0.1 to 0.35 milligrams per milliliter, and said local anesthetic is present in a concentration of about 0.2% to 0.4% by weight.

10. A method for the treatment of reflex sympathetic drystrophy comprising the intravenous regional co-administration of a haloalkylamine α adrenergic blocking agent and a local anesthetic wherein said haloalkylamine α adrenergic blocking agent is present in a concentration of about 0.05 to about 1.0 milligrams per milliliter and said local anesthetic is present in a concentration of about 0.1% to 0.5% by weight.

11. The method of claim 10 wherein said haloalkylamine α adrenergic blocking agent is selected from the group consisting of phenoxybenzamine and dibenamine.

12. The method of claim 10 wherein said local anesthetic is selected from the group consisting of procaine, bupivacaine, chloroprocaine, cocaine, cyclomethylcaine, dibucaine, dimethisoquin, dyclonine, hexylcaine, lidocaine, mepivacaine, phenacaine, piperocaine, pramoxine, prilocaine, proparacaine, tetracaine, procaine hydrochloride, bupivacaine hydrochloride, chloroprocaine hydrochloride, cocaine hydrochloride, cyclomethylcaine hydrochloride, dibucaine hydrochloride, dimethisoquin hydrochloride, dyclonine hydrochloride, hexylcaine hydrochloride, lidocaine hydrochloride, mepivacaine hydrochloride, phenacaine hydrochloride, piperocaine hydrochloride, pramoxine hydrochloride, prilocaine hydrochloride, proparacaine hydrochloride, tetracaine hydrochloride, cyclomethylcaine, cyclomethylcaine sulfate, benzocaine, butyl aminobenzoate, orthoform, naepaine, naepaine hydrochloride, benzoxinate, and benzoxinate hydrochloride.

13. The method of claim 10 wherein said haloalkylamine α adrenergic blocking agent is administered in an amount of about 1.5 to about 30 milligrams, and said local anesthetic is administered in an amount of about 3.75 to 150 milligrams.

14. A method for the treatment of regional sympathetic dystrophy comprising the intravenous regional co-administration of phenoxybenzamine and a local anesthetic selected from the group of lidocaine and procaine wherein said phenoxybenzamine is present in a concentration of about 0.05 to about 1.0 milligrams per milliliter, and said local anesthetic is present in a concentration of about 0.1% to 0.5% by weight.

15. The method of claim 14 wherein said local anesthetic is lidocaine.

16. The method of claim 14 wherein said phenoxybenzamine is administered in an amount of about 1.5 to about 30 milligrams, and said local anesthetic is administered in an amount of about 30 to about 250 milligrams.

17. The method of claim 14 wherein said phenoxybenzamine is administered in an amount of about 5 to about 10 milligrams, and said local anesthetic is administered in an amount of about 75 to about 125 milligrams.

18. A method for the treatment of regional sympathetic dystrophy comprising the intravenous regional administration of a local anesthetic to produce a period of anesthesia, followed by the intravenous regional administration of a haloalkylamine α adrenergic blocking agent during said period of anesthesia wherein said haloalkylamine α adrenergic blocking agent is present in a concentration of about 0.05 to about 1.0 milligrams per milliliter and said local anesthetic is present in a concentration of about 0.1% to 0.5% by weight.

19. The method of claim 18 wherein said local anesthetic is selected from the group consisting of procaine, bupivacaine, chloroprocaine, cocaine, cyclomethylcaine, dibucaine, dimethisoquin, dyclonine, hexylcaine, lidocaine, mepivacaine, phenacaine, piperocaine, pramoxine, prilocaine, proparacaine, tetracaine, procaine hydrochloride, bupivacaine hydrochloride, chloroprocaine hydrochloride, cocaine hydrochloride, cyclomethylcaine hydrochloride, dibucaine hydrochloride, dimethisoquin hydrochloride, dyclonine hydrochloride, hexylcaine hydrochloride, lidocaine hydrochloride, mepivacaine hydrochloride, phenacaine hydrochloride, piperocaine hydrochloride, pramoxine hydrochloride, prilocaine hydrochloride, proparacaine hydrochloride, tetracaine hydrochloride, cyclomethylcaine, cyclomethylcaine sulfate, benzocaine, butyl aminobenzoate, orthoform, naepaine, naepaine hydrochloride, benzoxinate, and benzoxinate hydrochloride.

20. The method of claim 18 wherein said haloalkylamine α adrenergic blocking agent is selected from the group consisting of phenoxybenzamine and dibenamine.

* * * * *